(12) United States Patent
Swedo

(10) Patent No.: US 9,371,497 B2
(45) Date of Patent: Jun. 21, 2016

(54) THPE ETHERS

(71) Applicant: Dow Global Technologies LLC, Midland, MI (US)

(72) Inventor: Raymond J. Swedo, Mount Prospect, IL (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 14/647,604

(22) PCT Filed: Nov. 27, 2013

(86) PCT No.: PCT/US2013/072135
§ 371 (c)(1),
(2) Date: May 27, 2015

(87) PCT Pub. No.: WO2014/088898
PCT Pub. Date: Jun. 12, 2014

(65) Prior Publication Data
US 2015/0344796 A1    Dec. 3, 2015

Related U.S. Application Data

(60) Provisional application No. 61/733,957, filed on Dec. 6, 2012.

(51) Int. Cl.
*C10L 1/185* (2006.01)
*C07C 43/20* (2006.01)
*C10L 1/00* (2006.01)
*C10L 1/18* (2006.01)

(52) U.S. Cl.
CPC .................. *C10L 1/003* (2013.01); *C07C 43/20* (2013.01); *C10L 1/18* (2013.01); *C10L 1/1852* (2013.01); *C10L 2200/0446* (2013.01); *C10L 2230/16* (2013.01); *C10L 2270/026* (2013.01)

(58) Field of Classification Search
CPC ........... C10L 1/003; C10L 1/85; C10L 1/185; C10L 1/1852; C07C 43/2044; C07C 43/264
USPC ..................... 44/447; 208/12, 15–17; 568/643
See application file for complete search history.

(56) References Cited

U.S. PATENT DOCUMENTS

| | | | | |
|---|---|---|---|---|
| 5,215,856 A | * | 6/1993 | Jayaraman ............ | G03F 7/0226 430/165 |
| 5,981,283 A | | 11/1999 | Anderson, II et al. | |
| 6,482,651 B1 | * | 11/2002 | Smith .................... | C07C 69/017 436/166 |
| 7,858,373 B2 | | 12/2010 | Banavali et al. | |
| 9,012,706 B2 | * | 4/2015 | Green ..................... | C07C 43/20 44/440 |
| 2004/0092738 A1 | | 5/2004 | Park et al. | |
| 2011/0251438 A1 | * | 10/2011 | Munnich ................. | C07C 37/82 568/720 |
| 2011/0289831 A1 | | 12/2011 | Green et al. | |
| 2015/0307795 A1 | * | 10/2015 | Green ..................... | C10L 1/003 44/442 |

FOREIGN PATENT DOCUMENTS

JP        1992199580 A    2/1994

OTHER PUBLICATIONS

EIC Search Apr. 2016.*
STN Search Apr. 29, 2016.*
Islam, et al., "Synthesis and Characterization of Branched Bisphenol-A Polycarbonates Functionalized with Siloxane", Macromolecular Research, vol. 19, No. 12, pp. 1278-1286 (2011).
J. Am. Chem. Soc. vol. 107, XP55105127, pp. 5545-5546 (1985).
Alisova, et al., "Simultaneous reaction of acetyl chloride with cyclohexene and phenetole in the presence of aluminum chloride", XP002721069 (1986).

* cited by examiner

*Primary Examiner* — Pamela H Weiss
(74) *Attorney, Agent, or Firm* — Kenneth Crimaldi

(57) ABSTRACT

A method for marking a petroleum hydrocarbon or a liquid biologically derived fuel. The method comprises adding to a petroleum hydrocarbon or a liquid biologically derived fuel at least one compound having formula (I),

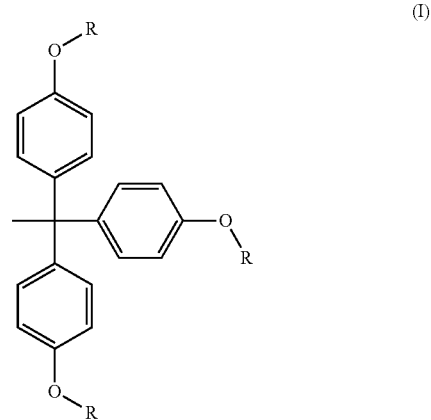

wherein R is $C_1$-$C_{12}$ alkyl, $C_3$-$C_{12}$ alkenyl or $C_7$-$C_{12}$ aralkyl; wherein each compound having formula (I) is present at a level from 0.01 ppm to 50 ppm.

7 Claims, No Drawings

THPE ETHERS

This invention relates to a method for marking liquid hydrocarbons and other fuels and oils, and compounds useful therein.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a method for marking a petroleum hydrocarbon or a liquid biologically derived fuel. The method comprises adding to a petroleum hydrocarbon or a liquid biologically derived fuel at least one compound having formula (I),

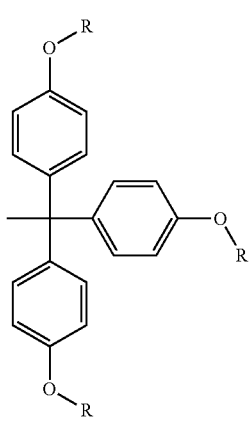

(I)

wherein R is $C_1$-$C_{12}$ alkyl, $C_3$-$C_{12}$ alkenyl or $C_7$-$C_{12}$ aralkyl; wherein each compound having formula (I) is present at a level from 0.01 ppm to 50 ppm.

The present invention further provides a compound having formula (I),

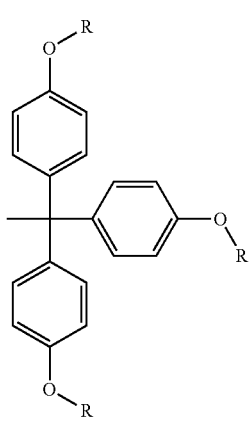

(I)

wherein R is $C_1$-$C_7$ alkyl, $C_3$-$C_{12}$ alkenyl or $C_7$-$C_{12}$ aralkyl.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a saturated, substituted or unsubstituted hydrocarbyl group having from one to twenty-two carbon atoms in a linear or branched arrangement. Substitution on alkyl groups of one or more hydroxy or alkoxy groups is permitted. Preferably, alkyl groups are unsubstituted. An "alkenyl" group is an alkyl group having at least one carbon-carbon double bond, preferably one carbon-carbon double bond. An "aryl" group is a substituent derived from an aromatic hydrocarbon compound. An aryl group has a total of from six to twenty ring atoms, unless otherwise specified, and has one or more rings which are separate or fused. Substitution on aryl groups of one or more alkyl or alkoxy groups is permitted. An "aralkyl" group is an "alkyl" group substituted by an "aryl" group. Preferably, the compounds of this invention contain elements in their naturally occurring isotopic proportions.

In the compound of this invention, preferably R is $C_1$-$C_6$ alkyl, $C_3$-$C_{12}$ alkenyl or $C_7$-$C_{12}$ aralkyl; preferably $C_2$-$C_6$ alkyl, $C_3$-$C_{12}$ alkenyl or $C_7$-$C_{12}$ aralkyl; preferably $C_2$-$C_6$ alkyl or $C_3$-$C_{10}$ alkenyl; preferably $C_2$-$C_6$ alkyl; preferably $C_3$-$C_6$ alkyl; preferably $C_4$-$C_6$ alkyl. Preferably alkyl, alkenyl and aralkyl substituents are unsubstituted. Preferably alkyl and alkenyl groups are linear.

In the method of this invention, preferably R is $C_1$-$C_{10}$ alkyl, $C_3$-$C_{12}$ alkenyl or $C_7$-$C_{12}$ aralkyl; preferably $C_2$-$C_{10}$ alkyl, $C_3$-$C_{10}$ alkenyl or $C_7$-$C_{12}$ aralkyl; preferably $C_2$-$C_{10}$ alkyl or $C_3$-$C_{10}$ alkenyl; preferably $C_2$-$C_{10}$ alkyl; preferably $C_3$-$C_{10}$ alkyl; preferably $C_4$-$C_{10}$ alkyl; preferably $C_4$-$C_8$ alkyl. Preferably alkyl, alkenyl and aralkyl substituents are unsubstituted. Preferably alkyl and alkenyl groups are linear.

In using the compounds disclosed herein as markers, preferably the minimum amount of each compound added to a liquid to be marked is at least 0.02 ppm, preferably at least 0.05 ppm, preferably at least 0.1 ppm, preferably at least 0.2 ppm. Preferably, the maximum amount of each marker is 30 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon or biodiesel fuel; preferably a petroleum hydrocarbon; preferably crude oil, gasoline, diesel fuel, kerosene, jet fuel or heating oil; preferably diesel fuel or gasoline; preferably diesel fuel.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds disclosed herein may be prepared by methods known in the art, e.g., alkylation of 1,1,1-tris(4-hydroxyphenyl)ethane (THPE) with an alkyl halide in the presence of base. For example, THPE ethers may be prepared according to the following reaction scheme,

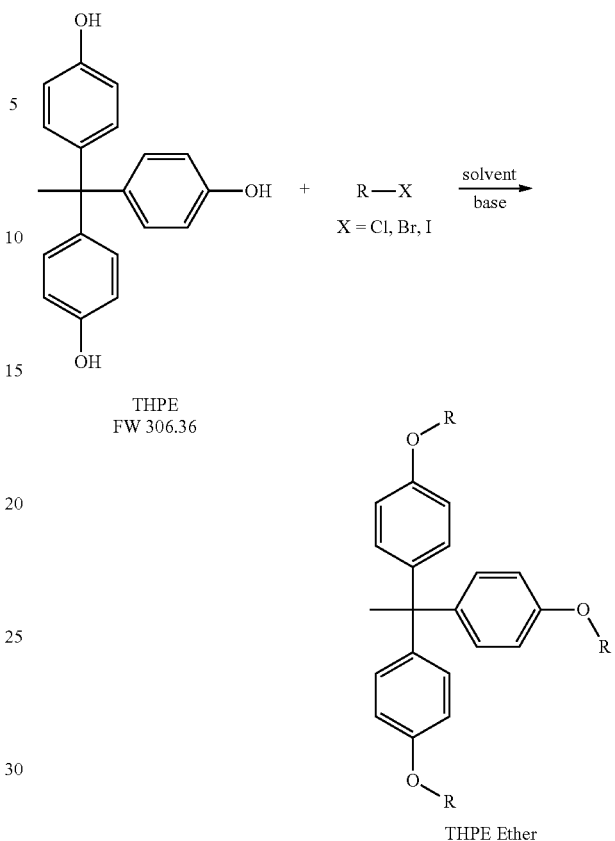

wherein R is as defined previously. Solvents which may be useful include, e.g., polar aprotic solvents. Suitable bases include, e.g., metal or tetraalkylammonium hydroxides or alkoxides.

EXAMPLES

General Synthesis Procedure:

A 100 mL 3-neck flask was equipped with a magnetic stirrer, a reflux condenser, a nitrogen blanket, and a heating mantle with a temperature controller and a thermocouple.

The flask was charged with 0.01 mole of 1,1,1-tris(4-hydroxyphenyl)ethane (THPE), 0.03 moles of potassium hydroxide (KOH) pellets, and 25 mL of dimethylsulfoxide (DMSO). The mixture was stirred under nitrogen and heated to 105° C. Stirring was continued until the KOH pellets dissolved. The solution was then cooled to 50° C. and 0.03 moles of alkyl halide (bromide or chloride) was added in one portion. A brief exotherm of from 5-10° C. was usually observed, then the temperature drops. The reaction mixture temperature was increased to 65° C., and the progress of the reaction followed by sampling periodically for GC analyses. When the reaction reached completion, the reaction mixture was cooled to below 50° C., then poured into about 300 mL of water containing a few pellets of KOH and several grams of sodium chloride. Toluene (about 100 mL) was added, and the mixture stirred at room temperature for about 30-60 minutes. The mixture was transferred to a separatory funnel and the layers were separated. The aqueous layer was extracted with 1×50 mL of toluene, and the toluene layers were combined. The toluene solution was washed with 1×75 mL of water and with 1×75 mL of saturated aqueous sodium chloride solution. The solution was dried over anhydrous magnesium sulfate, then the solvent was removed by rotary evaporation. The product THPE alkyl ethers were obtained as oils.

4,4',4''-(Ethane-1,1,1-triyl)tris(butoxy)benzene (THPE-4): 89.7% yield, >91% purity by GC. $^1$H-NMR: 0.957 ppm/triplet/intensity 9; 1,816-1.387 ppm/multiplet/intensity 11.43; 3.922 ppm/triplet/intensity 6.51; 6.998-6.745 ppm/multiplet/intensity 13.67; 2.093 ppm/singlet/intensity 2.52. $^{13}$C-NMR: 13.805, 19.223, 31.348, 67.444, 157.044, 113.501, 129.299, 141.607, 50.493, and 30.735 ppm. IR: 3037, 2955, 2933, 2870, 1607, 1578, 1508, 1469, 1291, 1248, 1180, 1052, 828, 639 cm$^{-1}$.

4,4',4''-(Ethane-1,1,1-triyl)tris(pentyloxy)benzene (THPE-5): 86.8% yield, >93% purity by GC. $^1$H-NMR: 0.920 ppm/triplet; 1.454-1.356 ppm/multiplet; 1.766 ppm/quartet; 2.095 ppm/singlet—combined intensity 30.63; 3.949 ppm/triplet/intensity 6.29; 6.998-6.745 ppm/intensity 13.95. $^{13}$C-NMR: 13.971, 22.421, 31.290, 28.209, 67.742, 157.052, 113.496, 129.499, 141.602, 50.493, and 30.739 ppm. IR: 3037, 2958, 2934, 2871, 1607, 1578, 1508, 1472, 1290, 1247, 1180, 1146, 1028, 876, 857, 828, and 605 cm$^{-1}$.

4,4',4''-(Ethane-1,1,1-triyl)tris(hexyloxy)benzene (THPE-6): 85.9% yield, >80% purity by GC. $^1$H-NMR: 0.897 ppm/triplet/intensity 9; 1.483-1.281 ppm/multiplet/intensity 17.36; 1.759 pm/quartet/intensity 4.46; 3.918 ppm/triplet/intensity 6.29; 6.998-6.746 ppm/multiplet/intensity 13.95; 2.095 ppm/singlet/intensity 2.49. $^{13}$C-NMR: 13.971, 22.545, 31.543, 25.709, 29.247, 67.776, 157.014, 113.496, 129.486, 50.476, and 29.247 ppm. IR: 3037, 2931, 2859, 1607, 1579, 1508, 1469, 1290, 1247, 1180, 1028, 829, and 606 cm$^{-1}$.

GC Analyses: Reaction progress was followed using a Hewlett Packard Model 6890 GC system with FID detector. The column was a J&W Scientific DB-5, 7.5 meter×0.25 mm×1μ film. Initial oven temperature was 50° C. with an initial hold time of 1 minute. This was followed by a temperature ramp up to 280° C. at 10° C./minute, with a final hold time of 15 minutes. The injector port and the detector were both at 275° C. The sample size was 1 μL, the helium carrier gas flow rate was 1 mL/minute, and the split ratio was 50:1.

IR Analyses: These were performed using a Nicolet 560 FTIR spectrometer. For liquid samples, a small drop was cast as a neat film between two KBr plates. The IR spectrum was acquired in the transmission mode from 4000 to 400 cm$^{-1}$, with a spectral resolution of 4 cm$^{-1}$. A Happ-Genzel type apodization function was used.

NMR Analyses: Both $^1$H- and $^{13}$C-NMR analyses were acquired using a Bruker 200 NMR spectrometer operating at 4.7 T. $^1$H-NMR spectra were obtained using an 8.2 second accumulation time and 2.0 KHz sweep width. The $^{13}$C-NMR spectra were obtained at a 4.7 second accumulation time and 7.0 KHz sweep width. Methanol-d$_4$ was typically used as the NMR solvent. Chemical shifts were referenced using the solvent resonances as 3.30 ppm for $^1$H-NMR, and at 59.05 pm for $^{13}$C-NMR.

GC/MS Analyses: Stock solutions of the THPE alkyl ethers were prepared in dichloromethane. These solutions were used to establish GC retention times and MS fragmentation patterns. GC/MS Parameters:

column: Agilent DB 35 m-15 meters×0.25 mm×0.25μ
 flow rate: 1.5 mL/minute He carrier gas
 initial oven temperature: 100° C.
 ramp 1: 20° C./minute to 280° C., then hold 10 minutes
 ramp 2: 20° C./minute to 340° C., then hold 6 minutes
 inlet temperature: 280° C.
 insert: splitless; vent: 15 minutes; single taper, glass wool, deactivated
 injection volume: 3 μL; viscosity: 5 seconds; plunger: fast
 mass transfer line temperature: 280° C.
 MS quad: 200° C.; MS source: 250° C.
 solvent delay: 18.5 minutes Solubility Studies: The solubility properties of the THPE alkyl ethers were determined by mixing 0.1 grams of THPE alkyl ether with 0.9 grams of solvent. The mixtures were warmed to 60° C. for a few minutes to ensure the formation of homogeneous solutions. The solutions were cooled to room temperature, then they were placed into a freezer at −10° C. The solutions were checked daily to see if any crystallization had occurred.

GC Retention Time, GC/MS, and Solubility Results:

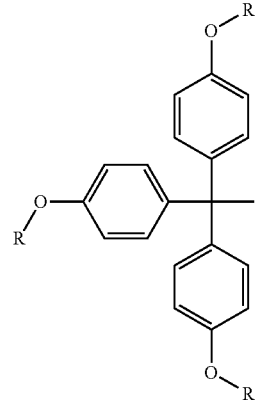

THPE Alkyl Ether

| R | GC Retention Time, min. | Major M/S Ion Masses | Solubility @ −10° C./ 7 Days |
|---|---|---|---|
| n-C$_4$H$_9$ | 21.72 | 459 | A, B, C, D |
| n-C$_5$H$_{11}$ | 23.72 | 501 | A, B, C, D |
| n-C$_6$H$_{13}$ | 26.38 | 543 | A, B, C, D |

A = 75:25 (v/v) Advasol 200H:cyclohexanone
B = 75:25 (v/v) Advasol 200H:o-sec-Butylphenol
C = 75:25 (v/v) Advasol 200H - naphthalene depleted:cyclohexanone
D = 75:25 (v/v) Advasol 200H - naphthalene depleted:o-sec-Butylphenol Advasol 200H is a mixed aromatic hydrocarbon solvent available from Advanced Aromatics.

Linearity and Reproducibility:
Linearity and repeatability of THPE-5 in Turkey diesel:

| Stock | Stock(mg/ml) | Sub(μg/ml) |
|---|---|---|
| THPE-5 | 1.62 | 9.71 |

40.44 mg in 25 ml DCM, 0.15 ml Stock in 25 ml Turkey Diesel

| Standard | 1 | 2 | 3 | 4 | 5 |
|---|---|---|---|---|---|
| Substock (μl) | 100 | 200 | 300 | 400 | 500 |
| THPE-5 (ppb) | 97.1 | 194.1 | 291.2 | 388.2 | 485.3 |

Linearity:

| Standard | Conc(ppb) | Area |
|---|---|---|
| 1 | 97.1 | 42150 |
| 2 | 194.1 | 86251 |
| 3 | 291.2 | 127366 |
| 4 | 388.2 | 167807 |
| 5 | 485.3 | 209809 |

Linear regression analysis of these points with concentration on the x-axis yielded a slope of 429.519 and a y-intercept of 1,614.40, with $R^2$=0.9998.

Repeatability:

| Replicate | Area | Conc. (ppb) |
|---|---|---|
| 1 | 118798 | 272.8 |
| 2 | 114157 | 262.0 |
| 3 | 110375 | 253.2 |
| 4 | 118687 | 272.6 |
| 5 | 116537 | 267.6 |
| 6 | 114857 | 263.6 |
| Avg. Conc. | | 265.3 |
| % Recovery | | 91.1 |
| Std Dev | | 7.4 |
| RSD | | 2.8 |

1. SIM: 501
2. Solvent: Turkey diesel #6
Oven: 100-20 C/min-280(10)-20 C/min-340(4), 3 μl,
Viscosity delay: 1 sec.
Solvent delay: 23 min
Split open: 20 min

The invention claimed is:

1. A method for marking a petroleum hydrocarbon or a liquid biologically derived fuel; said method comprising adding to a petroleum hydrocarbon or a liquid biologically derived fuel at least one compound having formula (I),

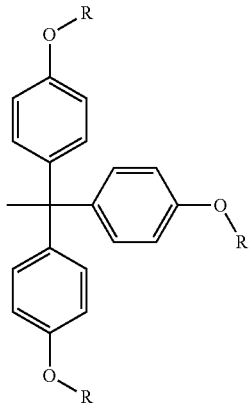

(I)

wherein R is $C_1$-$C_{12}$ alkyl, $C_3$-$C_{12}$ alkenyl or $C_7$-$C_{12}$ aralkyl; wherein each compound having formula (I) is present at a level from 0.01 ppm to 50 ppm.

2. The method of claim 1 in which R is $C_2$-$C_{10}$ alkyl or $C_3$-$C_{10}$ alkenyl.

3. The method of claim 2 in which each compound having formula (I) is present at a level from 0.02 ppm to 20 ppm.

4. The method of claim 3 in which R is $C_2$-$C_{10}$ alkyl.

5. The method of claim 4 in which each compound having formula (I) is present at a level from 0.05 ppm to 15 ppm.

6. The method of claim 5 in which R is $C_3$-$C_{10}$ alkyl.

7. A compound having formula (I),

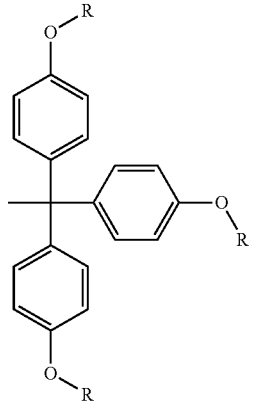

(I)

wherein R is $C_3$-$C_6$ alkyl.

* * * * *